United States Patent
Lu et al.

(10) Patent No.: US 9,512,072 B2
(45) Date of Patent: Dec. 6, 2016

(54) BIODEGRADABLE COMPUTED TOMOGRAPHY CONTRAST AGENTS

(71) Applicant: Case Western Reserve University, Cleveland, OH (US)

(72) Inventors: Zheng-Rong Lu, Beachwood, OH (US); Erlei Jin, Laramie, WY (US); Xiaohui Wu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 43 days.

(21) Appl. No.: 14/529,631

(22) Filed: Oct. 31, 2014

(65) Prior Publication Data

US 2015/0119706 A1    Apr. 30, 2015

Related U.S. Application Data

(60) Provisional application No. 61/898,021, filed on Oct. 31, 2013.

(51) Int. Cl.
| | |
|---|---|
| *A61K 49/04* | (2006.01) |
| *C07C 319/12* | (2006.01) |
| *C07C 323/25* | (2006.01) |
| *C07D 207/46* | (2006.01) |
| *C08G 2/00* | (2006.01) |

(52) U.S. Cl.
CPC ......... *C07C 323/25* (2013.01); *A61K 49/0438* (2013.01); *A61K 49/0442* (2013.01); *C07C 319/12* (2013.01); *C07D 207/46* (2013.01)

(58) Field of Classification Search
CPC ............... A61K 49/0438; A61K 49/0442; C07C 319/12; C07C 323/25; C07D 207/46; C08G 2/00
See application file for complete search history.

(56) References Cited

U.S. PATENT DOCUMENTS 4,367,216 A * 1/1983 Mutzel .................. C07C 391/00
                                                                424/9.452

OTHER PUBLICATIONS

Magnusson et al., "Contrast Enhancement of Pathologic Lymph Nodes Demonstrated by Computed Tomography," Acta Radiologica 30 (1989) Fasc. 3, 307-310.*

Anderson, N. G., et al. "Spectroscopic (multi-energy) CT distinguishes iodine and barium contrast material in MICE." European radiology 20.9 (2010): 2126-2134.
de Vries, Anke, et al. "Block-copolymer-stabilized iodinated emulsions for use as CT contrast agents." Biomaterials 31.25 (2010): Chapter 2.
Hallouard, François, et al. "Iodinated blood pool contrast media for preclinical X-ray imaging applications—a review." Biomaterials 31.24 (2010): 6249-6268.
Kao, Chen-Yu, et al. "Long-residence-time nano-scale liposomal iohexol for X-ray—based blood pool imaging." Academic radiology 10.5 (2003): 475-483.
Kim, Dongkyu, et al. "Antibiofouling polymer-coated gold nanoparticles as a contrast agent for in vivo X-ray computed tomography imaging." Journal of the American Chemical Society 129.24 (2007): 7661-7665.
Krause, Werner, Alexander Schonborn, and Karsten Rupp. "CT imaging with iopromide liposomes in a rabbit model." Journal of liposome research 21.3 (2011): 229-236.
Lu, Zheng-Rong, et al. "Polydisulfide Gd (III) chelates as biodegradable macromolecular magnetic resonance imaging contrast agents." International journal of nanomedicine 1.1 (2006): 31.
Zhou, Zhuxian, and Zheng-Rong Lu. "Gadolinium-based contrast agents for magnetic resonance cancer imaging." Wiley Interdisciplinary Reviews: Nanomedicine and Nanobiotechnology 5.1 (2013): 1-18.
Peng, Chen, et al. "PEGylated dendrimer-entrapped gold nanoparticles for in vivo blood pool and tumor imaging by computed tomography." Biomaterials 33.4 (2012): 1107-1119.
Rabin, Oded, et al. "An X-ray computed tomography imaging agent based on long-circulating bismuth sulphide nanoparticles." Nature materials 5.2 (2006): 118-122.
Sasser, Todd A., et al. "Segmentation and measurement of fat volumes in murine obesity models using X-ray computed tomography." J. Vis. Exp 62 (2012).
Trubetskoy, Vladimir S., et al. "Block-copolymer of polyethylene glycol and polylysine as a carrier of organic iodine: design of long-circulating particulate contrast medium for X-ray computed tomography." Journal of drug targeting 4.6 (1997): 381-388.
Wathen, Connor A., et al. "In vivo X-Ray computed tomographic imaging of soft tissue with native, intravenous, or oral contrast." Sensors 13.6 (2013): 6957-6980.

* cited by examiner

*Primary Examiner* — Paul A Zucker
*Assistant Examiner* — Mark Luderer
(74) *Attorney, Agent, or Firm* — Tarolli, Sundheim, Covell & Tummino LLP

(57) ABSTRACT

Biodegradable computed tomography (CT) contrast agents comprising a polyiodinated aryl contrast agent that is crosslinked by an organic disulfide are described herein. The contrast agents can be used to image a tissue region by administering an effective amount of the biodegradable CT contrast agent to a subject, allowing a sufficient amount of time for the biodegradable CT contrast agent to enter the tissue region, and performing x-ray computed tomography imaging of the tissue region of the subject.

16 Claims, 5 Drawing Sheets

BIODEGRADABLE COMPUTED TOMOGRAPHY CONTRAST AGENTS

CROSS-REFERENCE TO RELATED APPLICATIONS

This application claims the benefit of U.S. Provisional Application Ser. No. 61/898,021, filed Oct. 31, 2013, the disclosures of which are incorporated by reference herein.

GOVERNMENT FUNDING

This invention was made with government support under contract # EB000489 awarded by the National Institutes of Health. The government has certain rights in the invention.

BACKGROUND

X-ray computed tomography (CT) is one of the most commonly used clinical diagnostic imaging technologies. CT is effective to visualize hard tissues due to the inherent density differences between hard and soft tissues. With the assistance of proper contrast agents, CT can also provide high resolution three-dimensional images of soft tissues. Current clinical CT contrast agents are mainly biocompatible small molecular compounds containing heavy elements, such as iodine (Hallouard et al., Biomaterials 2010, 31:6249-68) and barium (Anderson et al., Eur Radiol 2010; 20:2126-34). Small molecular iodinated organic compounds are the most commonly used as intravenous contrast agents for cardiovascular CT imaging, including angiography and myocardial perfusion, image-guided intravascular intervention and cancer diagnosis.

There have been significant advancements in CT technology. Multidetector CT and dual-source CT have been developed and used to reduce the radiation dose and to improve both temporal and spatial resolution. In contrast, little process has been made to address the limitations of CT contrast agents. Current intravascular CT contrast agents are based on biocompatible and highly functionalized water-soluble triiodobenzene derivatives. These small molecular contrast agents do not have favorable pharmacokinetics and are rapidly cleared from the blood circulation. Heusner et al., Eur J Nucl Med Mol I 2007; 34:S294-S. Perfect timing of contrast injection is required to catch the first pass for CT angiography. High doses or multiple doses are often used to generate sufficient contrast enhancement for accurate diagnostic imaging. However, the use of the agents at high doses and multiple doses often induce dose-related toxic side effects. Their rapid clearance at high concentrations from blood circulation may cause acute kidney injury or renal failure. There is an unmet clinical need for safe and effective CT contrast agents that can provide effective CT contrast enhancement at reduced doses and minimize dose related toxic side effects.

The search for safer and effective X-ray contrast agents has been continued for over a century since the first clinical use of X-ray for medical imaging. Besides the small molecular iodinated contrast agents, various polymeric or nanoparticulate contrast agents containing heavy elements have been reported to improve the pharmacokinetics and effectiveness of the iodinated small molecular contrast agents. de Vries et al., Biomaterials, 2010; 31:6537-44. Iodinated contrast agents have been incorporated into biocompatible polymers, polymeric nanoparticles (Trubetskoy et al., J Drug Target 1997; 4:381-8), liposomes (Krause et al., J Liposome Res 2011; 21:229-36) and dendrimers (Peng et al., Biomaterials 2012; 33:1107-19), to prolong the blood circulation of the agents for effective blood pool imaging. Colloids or nanoparticles containing other heavy elements, including thorium, bismuth, gold and etc, have also been reported as effective CT contrast agents. These agents have prolonged vascular circulation and provide sharp blood vessel delineation essential for CT angiography. For example, colloidal thorium oxide (1-1,000 nm in size) was first used for clinical X-ray imaging in 1930s. However, the agent was terminated for intravenous use in 1950s because of its slow excretion from the body and consequent toxic sides, e.g. cancer and liver fibrosis and cirrhosis. Despite the advantages of the polymeric or nanosized contrast agents for CT blood pool imaging, no such an agent has been approved for clinical use since then because of the concerns of potential toxic side effects associated their slow excretion.

Rational design of CT contrast agents with controlled pharmacokinetics and excretion rates is critical to address the drawbacks of both iodinated small molecular CT contrast agents and nanosized contrast agents. The inventors recently designed and developed biodegradable macromolecular MRI contrast agents based on polydisulfides. Lu et al., Int J Nanomedicine. 2006; 1(1):31-40. These agents initially behave as macromolecular agents in the body and produce superior contrast enhancement in the blood pool and soft tissues. The disulfide bonds in the polymer backbone are then gradually reduced by endogenous thiols in plasma via disulfide-thiol exchange reaction to give oligomeric or smaller molecules, which are readily excreted via renal filtration after the imaging. As a result, the polydisulfide based MRI contrast agents produce prolonged blood pool enhancement as macromolecular contrast agents and excrete from the body as small molecular agents with minimal tissue retention. However, there remains a need for novel biodegradable CT contrast agents.

SUMMARY OF THE INVENTION

The inventors have prepared polydisulfides containing a traditional iodinated CT contrast agent in order to optimize the pharmacokinetics of the agent and improve its safety. Initially acting as a macromolecular agent and achieving sharp blood vessel delineation, the polydisulfides can be reduced by endogenous thiols via disulfide-thiol exchange reaction to oligomers that can be readily excreted via renal filtration. Short polyethylene glycol (PEG) chain was also introduced to the polymers to further modify the in vivo properties of the agents. Strong and prolonged vascular enhancement has been generated with two new agents in mice (5-10 times higher blood pool enhancement than iodinaxol). The polydisulfide agents gradually degraded and excreted via renal filtration. The gradual excretion process could prevent contrast-induced nephropathy. These results show that the biodegradable macromolecular CT contrast agents are promising safe and effective blood contrast agents for CT angiography and image-guided interventions.

DETAILED DESCRIPTION OF THE INVENTION

Figure 1:
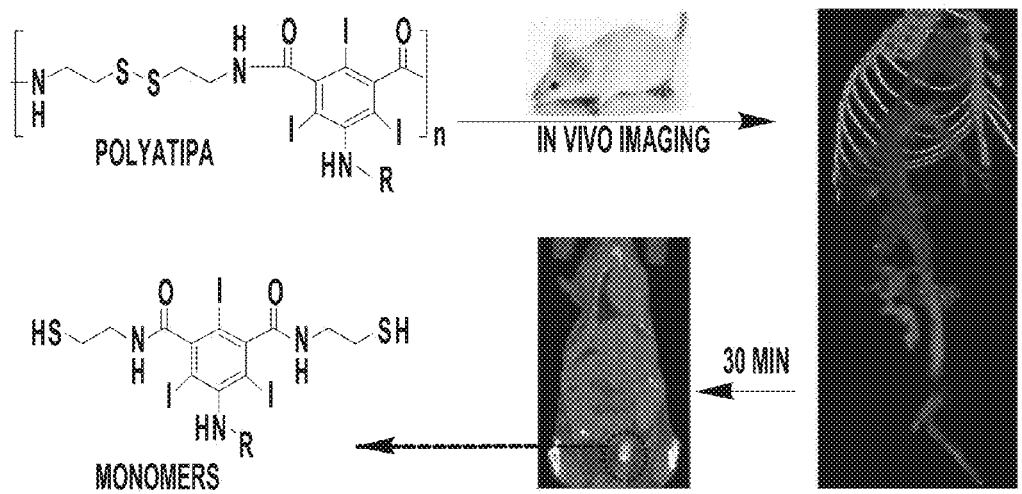
FIG. 1 provides a scheme illustrating the use of biodegradable macromolecular iodinated polymers as contrast agents (CAs) for computed tomography (CT) blood pool imaging. Initially acting as macromolecular agents and achieving clear and sharp vasculature images, the agents can be reduced by endogenous thiols to oligomers or monomers, which can be readily excreted via renal filtration.

The present invention provides iodinated polydisulfides that are safer and effective biodegradable macromolecular CT contrast agents. They will have prolonged blood circulation and limited vascular extravasation to produce strong blood pool enhancement. At the same time, the iodinated polydisulfides can be gradually reduced in the plasma by endogenous thiols to small iodinated oligomers, which can be gradually excreted via renal filtration. See FIG. 1. The gradual degradation of the agents can significantly slow down their renal excretion rate, reduce the concentration of the iodinated agents in the kidneys and minimize the acute assault to the kidneys, which is often caused by the conventional small molecular iodinated contrast agents. Consequently, these agents will have substantially lower toxic side effects on kidneys than the small molecular clinical CT agents. The iodinated polydisulfide-based biodegradable macromolecular CT contrast agents have improved pharmacokinetics and safety for effective contrast enhanced in vivo CT imaging.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for CT contrast agents are those that do not interfere with the compounds activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term "pharmacologically effective" is intended to qualify the amount of each agent which will achieve the goal improving the CT imaging of a tissue region while avoiding adverse side effects. The pharmacologically effective amount may be administered in one or more doses.

As used herein, the term "subject" refers to any animal (e.g., a mammal), including, but not limited to, humans, non-human primates, rodents, and the like, which is to be imaged by x-ray computed tomography. Typically, the terms "subject" and "patient" are used interchangeably herein in reference to a human subject.

The term "polymer" refers generally to a molecule of high relative molecular mass/weight, the structure of which includes repeat units derived, actually or conceptually, from molecules of low relative molecular mass (monomers). In general, a polymer is a compound having >1, and more typically >10 repeat units or monomer units. The term "oligomers," as used herein, refers to a relatively small polymer including from 1 to 10 monomers. In a number of embodiments, the biodegradable polymers of the contrast agents degrade into biocompatible degradation products.

The term "macromolecular," as used herein, refers to a large molecule commonly created by polymerization of smaller subunits, as opposed to non-polymerized small molecule organic compounds.

The term "biodegradable" as used herein refers to a polymer or contrast agent that can be broken down by either chemical or physical process, upon interaction with the physiological environment subsequent to use as an imaging agent, and erodes or dissolves within a period of time, typically within days, weeks or months. A biodegradable material serves a temporary function in the body, such as imaging a tissue region, and is then degraded or broken into components that are metabolizable or excretable.

One aspect of the invention provides a biodegradable computed tomography (CT) contrast agent comprising a polyiodinated aryl contrast agent that is crosslinked by an organic disulfide. Preferred polyiodinated aryl contrast agents are those based on a phenyl or diphenyl backbone. The term "polyiodinated," as used herein, refers to contrast agents including phenyl groups bearing from 2 to 4 iodine atoms. Examples of polyiodinated phenyl compounds are described, for example, in patents U.S. Pat. Nos. 3,097,228, 5,668,196, and 5,693,311, the disclosures of which are incorporated herein by reference. Specific examples of polyiodinated aryl contrast agents known to those skilled in the art include iopromide, iobitridol, iomeprol, iopamidol, iohexol, iodipamide, ioxaglate, and ioglycamic acid. In some embodiments, the polyiodinated aryl contrast agent used in the biodegradable CT contrast agent is 5-amino-2, 4,6-triiodoisophthalic acid (ATIPA).

In some embodiments, the biodegradable CT contrast agent has a structure based on a phenyl backbone according to formula I:

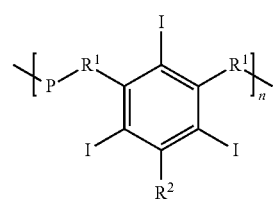

wherein P is an organic disulfide, R$^1$ is a carboxyl or carboxamide group, and R$^2$ is a an amine, a lower alkyl group, or an amine-bound water soluble polymer or oligomer, and n is from 2 to 10,000. In other embodiments, the biodegradable CT contrast agent has a structure based on a diphenyl backbone according to formula II:

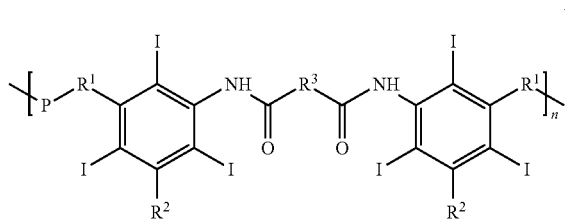

wherein P is an organic disulfide, R$^1$ is a carboxyl or carboxamide group, and R$^2$ is a an amine, a lower alkyl group, or an amine-bound water soluble polymer or oligomer, R$^3$ is a lower alkylene or alkylene ether group, and n is from 2 to 10,000.

In some embodiments, the polyiodinated aryl contrast agent includes an amine-bound water soluble polymer or oligomer. Examples of water soluble polymers and oligomers include polyols (e.g., polyethylene glycol), peptides (e.g., polylysine), and other hydrophilic polymers such as polyvinylpyrrolidone, dextran, polyethyleneoxide, and polyvinylalcohol. In some embodiments, the contrast agents are PEGylated. Water soluble polymers and/or oligomers can be introduced into the contrast agent in order to further modify the in vivo properties of the agents. More specifically, attachment of a water soluble polymer or oligomers (e.g., PEGylation) can improve the pharmacokinetics and prevent non-specific interaction of the contrast agents with the reticuloendothelial system. When preparing the PEGylated contrast agent, the PEG group can be added before polymerizing the contrast agent by forming polydisulfide. Preferably the PEG is attached to a suitable reactive site (e.g., an amine group) on the polyiodinated aryl contrast agent (e.g., ATIPA). Depending on the chemistry used to attach the PEG chain, a small intermediate compound may be present between the reactive site and the PEG chain. For example, when the PEG chain is attached using succinic anhydride, a succinate group may be present between the PEG chain and the reactive group of the polyiodinated aryl contrast agent. The water soluble polymer attached to the polyiodinated aryl contrast agent can have a variety of sizes. For example, a PEG chain can have an average molecular weight ranging from about 300 to about 1500 daltons.

The biodegradable CT contrast agents are polysulfides that are cross-linked by organic disulfides to improve the biodegradability of the contrast agent. In vivo, the polydisulfides that form the backbone of the biodegradable contrast agent are gradually reduced by endogenous thiols to form smaller polymers (i.e., oligomers) that can be readily excreted via renal filtration. The polydisulfide can be formed through polymerization with a variety of organic disulfides. Typically, the organic disulfides are aliphatic (e.g., alkyl) disulfides. Specific examples of organic disulfides suitable for use in forming polysulfides include cystamine, cystine, protected derivatives of the organic disulfides such as (Boc-cys-NHS)$_2$, and other organic disulfides such as oxidized glutathione. The polymerized CT contrast agents can vary in size. For example, the polymers can include from 2 to 10,000 monomers, where a monomer represents an organic disulfide bonded to a polyiodinated aryl contrast agent. In other embodiments, the polymers can have from 100 to 5,000 monomers, from 50 to 2,000 monomers, or from 10 to 500 monomers.

In some embodiments, the polydisulfide is formed using cystamine and the contrast agent has a structure according to formula III:

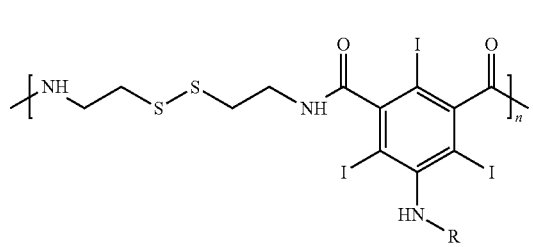

wherein R is a water soluble polymer or oligomer, and n is from 2 to 10,000.

In other embodiments, the polydisulfide is formed from cystine and the contrast agent has a structure according to formula IV:

wherein R is a water soluble polymer or oligomer and n is from 2 to 10,000.

A method for imaging a tissue region of a subject is described. The method includes the steps of (a) administering an effective amount of a biodegradable computed tomography (CT) contrast agent comprising a polyiodinated aryl contrast agent that is crosslinked by an organic disulfide to the subject; (b) allowing a sufficient amount of time for the biodegradable CT contrast agent to enter the tissue region; and (c) performing x-ray computed tomography imaging of the tissue region of the subject.

The method of imaging a tissue region includes the step of performing x-ray computed tomography imaging of the tissue region of the subject. X-ray computed tomography (CT) works by acquiring planar X-ray images or projections taken at various degrees of rotation around a patient or specimen. These data are then reconstructed, typically with a filtered back projection algorithm, to produce a three-dimensional array of radiodensity values. Frequently, these data are calibrated to Hounsfield units (HU) which indicate radiodensity. The calibrated Hounsfield scale will have values of −1,000 HU to represent air, 0 HU to denote water, and up to 3,000 HU for dense bone. Soft tissues, which are primarily composed of water and protein, will have densities in the +100 to +300 range and can be particularly difficult to differentiate via CT due to their low radio-opacity.

The major components of a conventional CT scanner are an x-ray tube and a detector array. Power is typically supplied by a high voltage generator controlled by scanner electronics and a scanner service module. A patient support and positioning couch is associated with the apparatus, and is moveable to transport the patient through the scanner. The scanner and voltage generator receive electronic commands from the operating console and transmit data to the computer system for image production and analysis. In addition, most CT scanners utilize computers to control the operation of the scanner.

There are several advantages to the use of X-ray CT for anatomical imaging. First, the tomographic data can be obtained with relative speed and ease. The actual scanning is completed in 0.5-5 minutes using equipment that is ubiquitously available at hospitals and most research institutions, though the procedure itself generally takes from 20 minutes to an hour to prepare the images and confirm that are of sufficient quality. There are a number of convenient and free software packages available for analysis and rendering of the CT data; for example ImageJ (NIH) (Abramoff et al., Biophotonics Int. 11, 36-42 (2004), Volview (Kitware Inc), and Amide (Loening A. M.; Gambhir, S. S. Mol. Imaging 2, 131-137 (2003). Next, CT imaging is non-invasive and, under the appropriate settings, the dose of radiation received from the scan will not harm, alter, or otherwise interfere with the biochemistry or life cycle of subjects. A further benefit of the X-ray CT modality is the

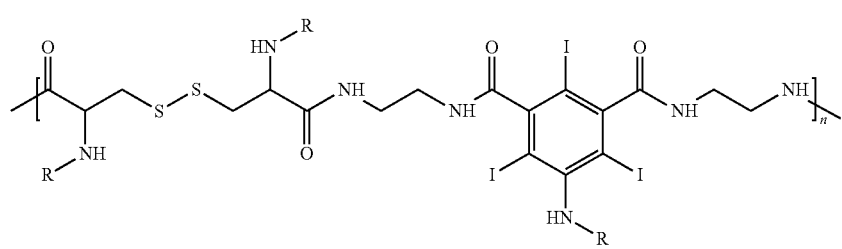

high-resolution data that are collected. Since clinical scanners are examining relatively large anatomical structures within patients, a 1 mm resolution is sufficient for diagnosis. However, higher resolution is required for pre-clinical research due to the much smaller size of rat or mouse anatomy. Scanners suitable for pre-clinical research are typically in the 30-300 μm range and are sometimes called microCT.

X-ray contrast agents are compounds with high electron density that will attenuate X-rays. Many contrast agents will perfuse or preferentially concentrate at a specific tissue, thus enabling its visualization and differentiation from surrounding sites. With the aid of these contrast agents, visualization of specific organs is greatly improved, which consequently leads to recognition of anatomical abnormalities, and in some cases, functional changes in rates of perfusion or clearance during studies of disease progression.

One aspect of the invention includes administering an effective amount of a biodegradable computed tomography CT contrast agent comprising a polyiodinated aryl contrast agent that is crosslinked by an organic disulfide to the subject. The polyiodinated aryl contrast agent administered can be any of the compounds described herein. For example, in some embodiments, the administered biodegradable CT contrast agent has a structure according to formula I:

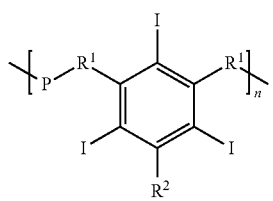

I wherein P is an organic disulfide, $R^1$ is a carboxyl or carboxamide group, and $R^2$ is a an amine, a lower alkyl group, or an amine-bound water soluble polymer or oligomer, and n is from 2 to 10,000.

In another embodiment, the administered biodegradable CT contrast agent has a structure according to formula II:

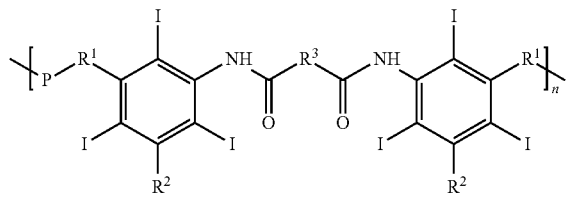

II wherein P is an organic disulfide, $R^1$ is a carboxyl or carboxamide group, and $R^2$ is a an amine, a lower alkyl group, or an amine-bound water soluble polymer or oligomer, $R^3$ is a lower alkylene or alkylene ether group, and n is from 2 to 10,000. Other embodiments of the invention include administration of the various biodegradable CT contrast agents described herein.

Once the biodegradable CT contrast agent has been administered, a sufficient amount of time for the biodegradable CT contrast agent to enter the tissue region. The time required for contrast agents to reach a tissue region are known by those skilled in the art, and can be calculated based on available software, and vary depending on the injection site and the particular tissue region. When planar X-ray images are acquired, tissues and other materials will attenuate X-rays based upon their own unique radio-opacity and composition. In general, structures that are denser and contain large quantities of electron rich elements absorb greater amounts of X-rays, while less dense materials absorb smaller amounts. The contrast noted in the planar X-ray projections will translate to the computed tomography data to enable the visualization of several types of tissue using the innate properties of the anatomy under observation. Bone, which is radio-dense and rich in calcium, absorbs large amounts of X-ray radiation and provides the highest natural X-ray attenuation. Lung tissue is distinguishable owing to the presence of air within its cavity, thus yielding significantly lower densities than the surrounding soft tissue and bone. Adipose is high in fatty acids and is slightly less dense than adjacent soft tissue, which enables its recognition via segmentation with the use of the proper software. Sasser et al., J. Vis. Exp. 62, e3680 (2012). Finally, brain tissue is generally homogenous on a CT, but its location is circumscribed by cranial bone and the tissue may be directly observed for changes occurring during disease progression. Aggarwal, et al., Neuroscience 162, 1339-1350 (2009).

Accordingly, the biodegradable CT contrast agents of the present invention can be used to image a wide variety of different types of tissue regions. Examples of different types of tissue regions include portions of the cardiovascular system, such as the heart, blood vessels, carotid arteries, and the aorta; lung tissue, adipose tissue, brain tissue, hepatic tissue, and renal tissue. All of these tissues can readily be imaged by injection of the biodegradable CT contrast agents. Note that while biodegradable CT contrast agents are typically used to image a particular tissue region of interest, they can also be used to image an organ, or a whole body.

The biodegradable CT contrast agents of the present invention can be used to image both healthy and diseased tissue. Examples of diseases tissue include ischemic tissue and tumor tissue. Examples of various types of cancer that can be imaged using the biodegradable CT contrast agents include colon cancer, lung cancer, kidney cancer, pancreas cancer, endometrial cancer, thyroid cancer, oral cancer, ovarian cancer, laryngeal cancer, hepatocellular cancer, bile duct cancer, squamous cell carcinoma, prostate cancer, breast cancer, cervical cancer, colorectal cancer, melanomas and any other tumors. Solid tumors, such as sarcomas and carcinomas can include, but are not limited to, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (e.g., a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). Preferred types of cancer include those resulting in solid tumors.

The biodegradable CT contrast agents will persist for long enough to carry out the CT imaging procedure. Accordingly, the imaging agents will persist for at least one hour, and in some cases, up to two hours, for images to be obtained, processed, and their quality confirmed. However, because the CT contrast agents of the invention are biodegradable, they will begin to deteriorate after the imaging procedure so that they are excreted and exhibit minimal tissue retention.

Administration and Formulation of Biodegradable CT Contrast Agents

In one aspect, the composition for administration comprises a contrast agent of the invention in a pharmaceutically acceptable carrier, e.g., an aqueous carrier. A variety of carriers can be used, e.g., buffered saline and the like. These solutions are sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected.

Administration of the contrast agent for in vivo imaging of a tissue, an organ or a full body can include a) providing a pharmaceutical formulation comprising the contrast agent of the invention and a pharmaceutically acceptable excipient, wherein the contrast agent is formed according to any of the above described embodiments, and wherein the formulation is suitable for administration as an imaging enhancing agent and the contrast agent is present in an amount sufficient to enhance a computed tomography (CT) image; b) providing an imaging device (i.e., a computed tomography (CT) device); c) administering the pharmaceutical formulation in an amount sufficient to generate the tissue or body image; and d) imaging the distribution of the pharmaceutical formulation of step a) with the imaging device, thereby imaging the tissue, organ or body.

The pharmaceutical formulations of the invention can be administered in a variety of unit dosage forms, depending upon the particular tissue or cancer to be imaged, the general medical condition of each patient, the method of administration, and the like. Details on dosages are well described on the scientific and patent literature. The exact amount and concentration of contrast agent or pharmaceutical of the invention and the amount of formulation in a given dose, or the "effective dose" can be routinely determined by, e.g. the clinician. The "dosing regimen" will depend upon a variety of factors, e.g. whether the tissue region or tumor to be imaged is disseminated or local, the general state of the patient's health, age and the like. Using guidelines describing alternative dosing regimens, e.g. from the use of other imaging contrast agents, the skilled artisan can determine by routine trials optimal effective concentrations of pharmaceutical compositions of the invention.

The pharmaceutical compositions of the invention can be delivered by any means known in the art systematically (e.g. intravenously), regionally or locally (e.g. intra- or peritumoral or intracystic injection, e.g. to image bladder cancer) by e.g. intraarterial, intratumoral, intravenous (iv), parenteral, intrapneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs). For example intra-hepatic artery injection or intracarotid artery injection. If it is decided to deliver the preparation to the brain, it can be injected into a carotid artery or an artery of the carotid system of arteries (e.g. ocipital artery, auricular artery, temporal artery, cerebral artery, maxillary artery etc.).

Preparation of the Compounds

Another aspect of the invention provides a method of making a biodegradable computed tomography (CT) contrast agent. Overall, the method includes the steps of reacting a polyiodinated aryl group with an organic disulfide to provide an iodinated aryl polysulfide contrast agent. In some embodiments, the method also includes the step of reacting a polyiodinated aryl group with a water soluble polymer or oligomers (e.g., polyethylene glycol) in order to provide, for example, a PEGylated polyiodinated aryl group, which can then be further reacted with an organic disulfide to provide a biodegradable CT contrast agent. The various intermediates, solvents, and reagents can vary to achieve the desired reactions.

In some embodiments, method includes the steps of: (a) reacting a dicarboxyl polyiodinated aryl group with an acyl chloride (e.g., thionyl chloride) to provide a diacyl chloride iodinated aryl group; and (b) polymerizing the diacyl chloride iodinated aryl group with an organic disulfide (e.g., cystamine or a cystine) to provide an iodinated aryl contrast agent that is crosslinked by an organic disulfide (e.g., cystamine or a cystine). Active esters and coupling agents can be used to facilitate the reaction. In further embodiments, the dicarboxyl polyiodinated aryl group is 5-amino-2,4,6-triiodoisophthalic acid (ATIPA). In yet another embodiment, the dicarboxyl polyiodinated aryl group is PEGylated 5-amino-2,4,6-triiodoisophthalic acid (ATIPA).

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Rational Design of Biodegradable Iodinated Polydisulfides as Safer Contrast Agents for CT Angiography Herein the inventors describe the synthesis and evaluation of novel iodinated polydisulfides as biodegradable CT blood pool contrast agents. A clinical iodinated CT contrast agent, 5-amino-2,4,6-triiodoisophthalic acid (ATIPA), was used as a monomer to copolymerize with cystamine to give iodinated polydisulfides, polyATIPA. The polydisulfides was further modified with a biocompatible polymer, polyethylene glycol (PEG$_{550}$), by pegylation at the amino group of ATIPA to optimize their pharmacokinetics and to prevent non-specific interaction with the reticuloendothelial system (RES). Hoffman et al., Acad Radiol 2003; 10:475-83. The degradability of the polydisulfides was investigated in vitro with the presence of cysteine and in vivo by analyzing the urine samples with mass spectrometry. The dynamic contrast enhanced CT imaging of the iodinated polydisulfides was assessed in mice on a micro-CT scanner with a clinical agent as a control. The renal safety of the pegylated iodinated polydisulfides was preliminarily assessed by histological analysis of the major organs after exposure to the agent.

EXPERIMENTAL

Materials

Poly(ethylene glycol) methyl ether (Mn=$_{550}$, PEG$_{550}$) 5-Amino-2,4,6-triiodoisophthalic acid (ATIPA), Maleic anhydride, thionyl chloride (SOCl$_2$), cystamine were purchased from Aldrich (St. Louis, Mo.). N,N-Dimethylformamide (DMF), triethylamine (TEA), Dimethyl sulfoxide (DMSO) and dichloromethane (DCM) were purchased from Fisher (St. Louis, Mo.) and dried over 4 Å molecular sieves.

Synthesis

Synthesis of PEG$_{550}$-Acid. PEG$_{550}$, (11 g, 20 mmol) was dissolved in 30 mL of anhydrous THF. Succinic anhydride (4 g, 40 mmol) was added into the solution. The mixture was stirred at room temperature for 48 h. THF was removed under vacuum and the rude product was redissolved in DCM and washed with water for 3 times. The solution was dried and pure product was obtained after remove the DCM under vacuum (10.5 g, yield 81%). $^1$H-NMR (400 MHz, CDCl3): δ (ppm): 4.26 (t), 3.67-3.62 (br), 3.37 (s), 2.64 (t).

Synthesis of PEG$_{550}$-Chloride. PEG$_{550}$-acid, (6.5 g, 10 mmol) was dissolved into 30 mL of anhydrous DCM. SOCl$_2$ (5 mL) and a drop of DMF were added into the solution and the mixture was stirred at room temperature for 20 h. The solvent and excess of SOCl$_2$ were removed under vacuum to obtain the chloride (6.5 g, yield 98%). $^1$H-NMR (400 MHz, CDCl3): δ (ppm): 4.25 (t), 3.68-3.61 (br), 3.37 (s), 3.20 (t), 2.68 (t).

Synthesis of PEG$_{550}$-ATIPA. ATIPA (5.84 g, 10 mmol) was suspended in 20 mL of DI water. NaOH (1 g, 25 mmol) was added into the solution to make the solution clear. At 0° C., PEG$_{550}$-chloride (6.5 g, 12 mmol) was added to the solution dropwise and NaOH (2 M) solution was added at the same time to keep the pH value at around 10. The mixture was stirred at 0° C. for 2 h then RT overnight. Water was removed under vacuum and pure product was purified through silicone gel column (DCM:methanol=5:1) (9.8 g, yield 81%). $^1$H-NMR (400 MHz, d-Acetone): δ (ppm): 4.26-4.23 (br), 3.68-3.61 (br), 3.37 (s), 2.68 (br).

Synthesis of PEG$_{550}$-ATIPC. PEG$_{550}$-ATIPA (12.3 g, 10 mmol) was dissolved in 20 mL of anhydrous DCM. 10 mL of thionyl chloride was added into the mixture and 2 drops of DMF was added as catalyst. The mixture was refluxed at 80° C. overnight. The solvent was removed under vacuum to obtain the final product (11.5 g, yield 92%). $^1$H-NMR (400 MHz, d-Acetone): δ (ppm): 4.26-4.23 (br), 3.68-3.61 (br), 3.37 (s), 2.80-2.68 (br).

Synthesis of the ATIPC chloride. 5-Amino-2,4,6-triiodoisophthalic acid (ATIPA, 28 g, 50 mmol) was added into 50 mL of anhydrous toluene. 30 mL of thionyl chloride was added into the mixture and 2 drops of DMF was added as catalyst. The mixture was refluxed at 80° C. for 12 h and TLC showed that there is no acid left. The solvent was removed under vacuum to obtain the crude product as yellow solid powder. The solid was recrystallized with anhydrous ethyl acetate twice to obtain the pure chloride (25 g, yield 83%). Characterized with MALDI TOF and HPLC.

Synthesis of the polyATIPA. At 16° C., cystamine (160 mg, 1.05 mmol) was dissolved in the mixture solvents of 1 mL of anhydrous DMSO and 0.5 mL of TEA. ATIPC powder (630 mg, 1 mmol) was added portion by portion into the mixture during 1.5 h. The mixture was stirred at this temperature for 6 h and put into 60° C. oil bath for another 12 h. After that, the mixture was dissolved into 20 mL of deionized water and put into a dialysis bag (MWO 6000-8000), dialyzed against deionized water, and then lyophilized (480 mg, yield 63%). $^1$H-NMR (400 MHz, d-DMSO): δ (ppm): 3.5-3.3 (br). PolyPEG$_{550}$ATIPA was obtained with the same method.

FPLC and Reverse-Phase HPLC

All the polymers were characterized by size exclusion chromatography (SEC) on an AKTA FPLC system (Amersham Biosciences Corp., Piscataway, N.J.) equipped with a Superose 12 column and a refractive index detector. Molecular weights were calibrated with standard poly[N-(2-hydroxypropyl)methacrylamide]. Ion-pairing reverse-phase HPLC (Agilent 1100, Santa Clara, Calif.) was performed with a RP-C18 HPLC column (4.6×250 mm$^2$, 5 μm particle size) and UV detector. The mobile phase was a gradient of 10-50% of acetonitrile aqueous solution containing 0.5% TFA at a total flow rate of 1 mL/min. An aliquot of 200 μL sample at approximately 0.1 mg/mL was injected, of which 20 μL went into the column at 25° C. The UV absorption peaked at 210 nm of the elution was recorded for analysis.

Evaluation of the In Vitro CT Values

All the samples were scanned on a small-animal PET/SPECT/CT system (Inveon, Siemens) with x-ray energy 0-80 kVp and a detector with the field of view 2048 mm×2048 mm. The images were obtained at an x-ray voltage of 80 kVp, an anode current of 500 μA and an exposure time of 200 ms for every rotational steps (total rotation degree is 360 and rotation steps are 180). The field of view was 2048 mm×2048 mm. Images were reconstructed on a 512 pixel×512 pixel grid with a pixel size of 66.7 μm×66.7 μm. The polymeric contrast agents were scanned at the concentration of 37.5, 75, 150 and 300 mg-I/mL compared with iodixanol. Deionized water was used as the control (0 HU).

Degradation of Polymers

The degradability of the polymer was investigated by the incubation of polymer with DL-homocysteine under physiological conditions. Mohs et al., Biomacromolecules 2005; 6:2305-2311. The DL-homocysteine concentration was 15 μM, mimicking the thiol concentration in the plasma. The concentration of polymers was 9.19 mM representing the iodine concentration 27.56 mM (350 mg-I/Kg) based on an average Balb/c mouse weighing 20 g. The polymer solution was put into a dialysis bag (MWO 6000) and incubated with of 15 μM DL-homocysteine solution (1 L×3) at 37° C. The UV absorption was detected at 240 nm. The molecular change of the polymer was traced by FPLC.

In Vivo Blood Pool CT Imaging

The polymeric contrast agents and the control contrast agent, iodixanol, were evaluated with BALB/c mice (18-22 g body weight, 6 mice per agent). All the mice were scanned on the same machine as the in vitro detection. The images were obtained at an x-ray voltage of 80 kVp, an anode current of 500 μA and an exposure time of 200 ms for every rotational steps (total rotation degree is 360 and rotation steps are 180). The field of view was 1024 mm×2048 mm. Images were reconstructed in a 1024 pixel×1024 pixel grid with a pixel size of 18 μm×18 μm. Each group was anesthetized by intramuscular injection of ketamine (35 mg/kg) and xylazine (8 mg/kg); anesthesia will be maintained by isoflurane inhalation. The contrast agent dose for each mouse was 350 mg-I/kg. The acquisition times were pre-injection and at 10, 20, 30, 45, and 60 min post-injection.

In Vivo Degradation

BALB/c mice were injected the contrast agent (PolyATIPA) at the concentration 27.56 mM (350 mg-I/Kg). Their urine was collected at 10, 20, 30, 45, 60, 90 and 120 min post-injection by pushing bladders. The in vivo degradation was analyzed through MALDI-TOF mass spectrometry.

CT Image Analysis

CT values are expressed in Hounsfield Units (HU) and were obtained per organ by drawing volumetric regions of interest (RIOs). Aviv et al., Biomaterials 2009; 30:5610-5616. The average HU values and the standard deviation were calculated from the data with 3 ROIs per organ. The CT data was analyzed to determine the contrast enhancement of different agents at various time points post-injection. In vivo CT values of the regions of interest, such as heart, blood, liver and bladder, were measured to study the dynamic enhancement of different organs. The dynamic enhancement of the blood showed the efficiency of the polymers used as blood pool contrast agents. The dynamic enhancement of the bladder indicated how fast the contrast agents will degrade and be excluded from the body.

Histochemical Analysis

After CT imaging, the mice were sacrificed under anesthetic conditions, and tissues of interest (lung, kidney, liver, spleen and heart) were excised and fixed in 10% neutral buffered formalin (10% NBF) [41]. For haematoxylin and eosin (H&E) staining, formalin fixed tissues from each organ were embedded into paraffin and paraffin-embedded tissues were sectioned into 4 μm thickness. Each histological section was documented by a dissecting microscope. The results were analyzed to evaluate the safety of the contrast agents to the organs.

Statistical Analysis

Statistical calculations will be performed using Prism (Graphpad Software, Inc). The data will be analyzed by repeated-measures two-way ANOVA using Bonferroni's post-test, assuming statistical significance at $p<0.05$.

Results and Discussion

Synthesis

Figure 2:
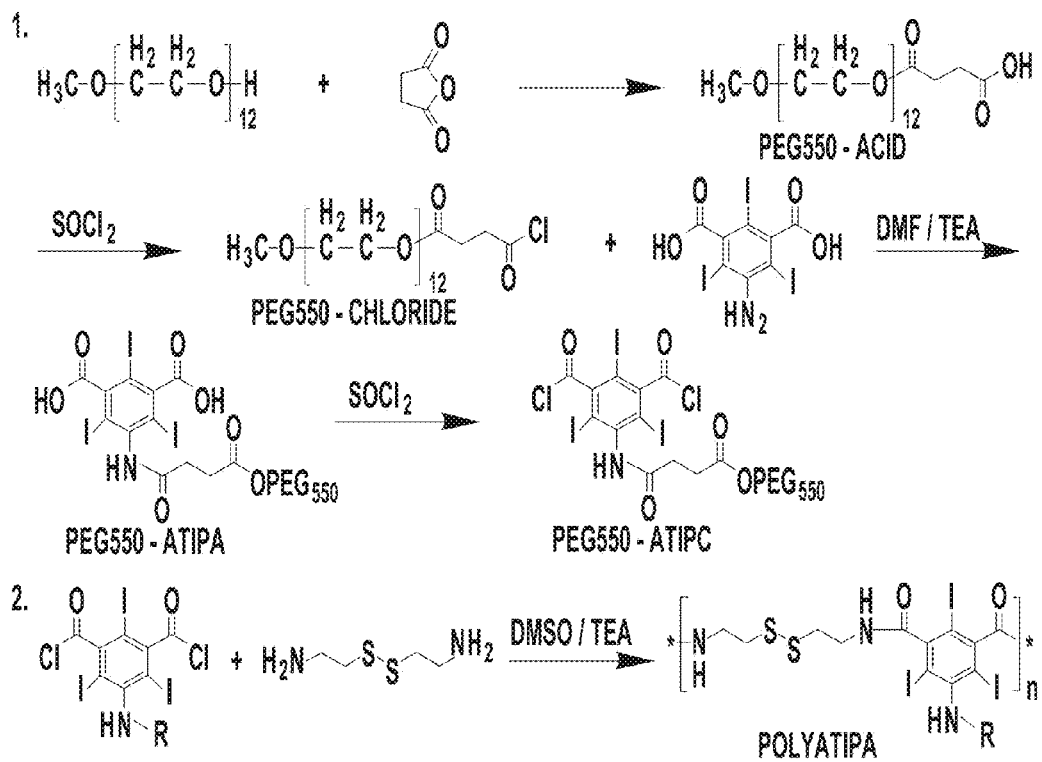
FIG. 2 provides a scheme showing the synthesis of biodegradable polymeric contrast agents including cystamine 1, synthesis of the monomer of polyPEG550ATIPA; 2, polymerize the iodinated monomers with cystamine. PolyATIPA, R=H; polyPEG550ATIPA, R=PEG550.
Figure 3:
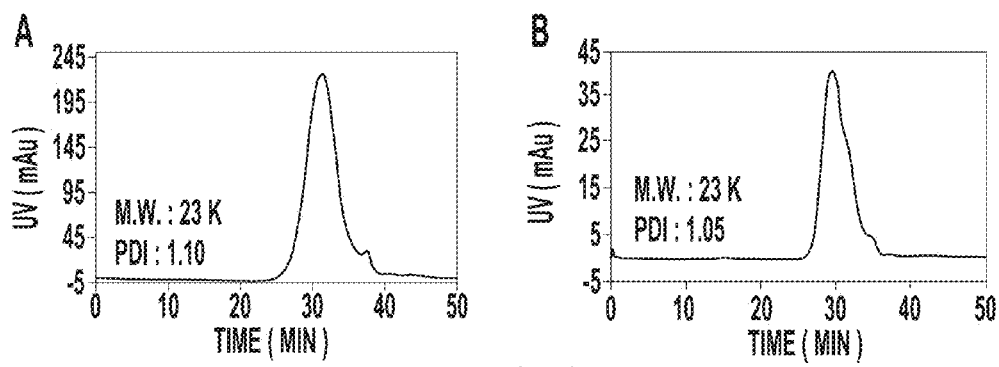
FIG. 3 provides size exclusion chromatograms of polyATIPA (A) and polyPEG550ATIPA (B).

Synthesis of two biodegradable polymeric iodinated contrast agents, polyATIPA and pegylated polyATIPA (polyPEG$_{550}$ATIPA), is shown in FIG. 2. First, two carboxylic groups of ATIPA were converted to acyl chlorides by reacting with thionyl chloride. The ATIPA acyl chloride was then polymerized with cystamine to produce the iodinated polydisulfides. For the synthesis of the pegylated contrast agent, PEG$_{550}$ was first conjugated to the amino group of ATIPA to produce a pegylated ATIPA. MethoxyPEG$_{550}$ was reacted to succinic anhydride to convert the hydroxyl group to a carboxylic group at the end. This carboxylic group was converted to acyl chloride, and then reacted with ATIPA to form the pegylated monomer PEG$_{550}$ATIPA. PEG$_{550}$ATIPA was similarly converted to acyl chloride and was finally polymerized with cystamine to give polyPEG$_{550}$ATIPA. After polymerization, the products were dialyzed with a membrane (MWCO=8,000 Da) against deionized water to remove the small molecular weight compounds and oligomers. The polymers were further purified with size exclusion chromatography using G50 Sephadex column eluted with deionized water. The polymer fractions were collected and lyophilized to give off-white solid products. The final polymers were characterized with NMR and size exclusion chromatography (FIGS. 3A and B). The number and weight averaged molecular weights of polyATIPA were 21 and 23 KDa, and 22 and 23 KDa for polyPEG$_{550}$ATIPA. Both iodinated polydisulfides had good water solubility.

Figure 4:
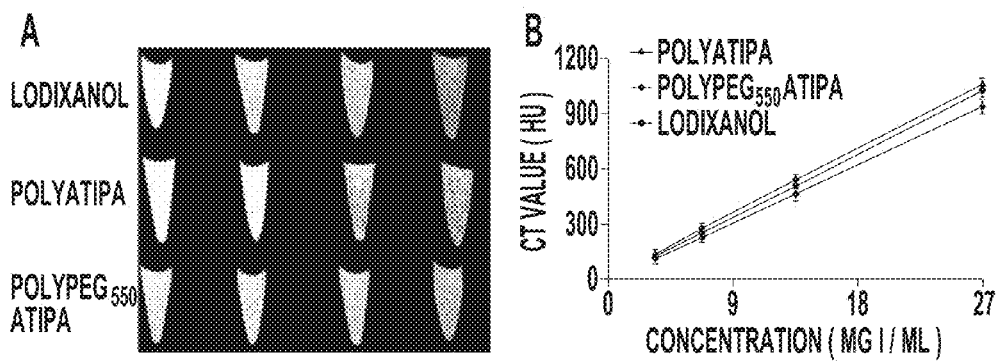
FIG. 4 provides the in vitro CT images of iodixanol, polyATIPA and polyPEG550ATIPA in the equivalent iodine concentrations (A) and X-ray attenuation of iodixanol, polyATIPA and polyPEG550ATIPA as a function of the concentration (B).

FIG. 4A shows the CT images of iodixanol, polyATIPA and polyPEG$_{550}$ATIPA at the equivalent iodine concentrations ranging from 37.5 to 300 mg-I/mL. All agents showed concentration dependent X-ray attenuation. The CT values of different concentrations were measured to compare the effectiveness of the contrast agents for X-ray attenuation. FIG. 4B shows the X-ray attenuation as a linear function of iodine concentration of the agents. PolyATIPA had higher HU values than the clinical contrast agent iodixanol, especially at high iodine concentration. High iodine content per molecule in polyATIPA could contribute to increase X-ray attenuation of the agent. In contrast, polyPEG$_{550}$ATIPA exhibited lower HU values than iodixanol possibly due to pegylation. PEG was reported as a negative CT contrast agent. The presence of PEG in polyPEG$_{550}$ATIPA may diminish the X-ray attenuation ability of the agent.

In Vitro Degradation

Figure 5:
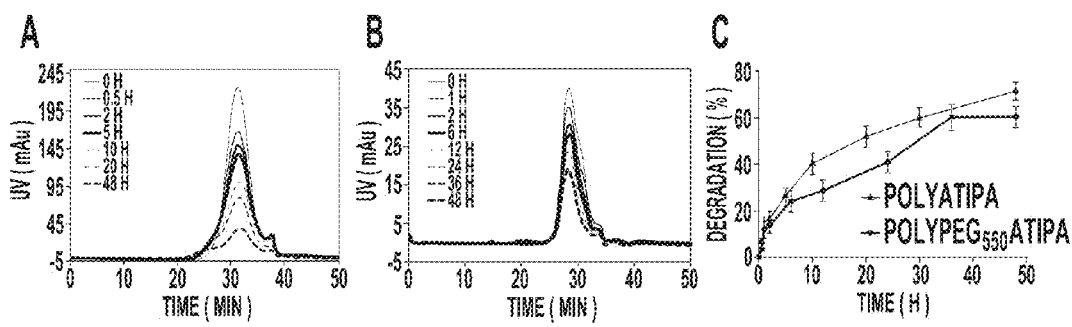
FIG. 5 provides graphs showing the in vitro degradation of the polymers. (A) The molecular weight distribution of polyATIPA (27.56 mM-I) in the incubation with 15 μM cysteine in PBS buffer (pH 7.4) at 37° C. (B) The molecular weight distribution of polyPEG550ATIPA (27.56 mM-I) in the incubation with 15 μM cysteine in PBS buffer (pH 7.4) at 37° C. (C) The degradation kinetics curves of contrast agents in PBS buffer (pH 7.4) at 37° C. (determined by UV at 240 nm).

The degradability of the iodinated polydisulfides was investigated by incubating the polymers with cysteine under physiological conditions. The polymer solutions were put into a dialysis bag with MWCO of 6,000 Da and incubated with 15 μM cysteine solution at 37° C. The cysteine concentration was used to mimic the thiol concentration in the plasma. The concentration of the polymers was 27.56 mM of iodine mimicking the initial plasma iodine concentration of the agents in an average Balb/c mouse weighing 20 g at a dose of 350 mg-I/Kg. Samples were taken at 0.5, 2, 5, 10, 20 and 48 hr and analyzed by SEC on an AKTA FPLC system equipped with a Superose 12 column and a UV detector. FIGS. 5A and 5B shows the gradual disappearance of the polymer peaks in the presence of cysteine due to the reduction of the disulfide bonds in polymer chains. Because of the dialysis method used here, the low molecular weight fractions could not be detected in the polymer samples. However, the decrease of the height of polymer peaks indicated the degradation of the polymers. FIG. 5C shows the degradation kinetics of contrast agents determined by UV spectrometry at 240 nm (according to standard sample). It appears that degradation of polyPEG$_{550}$ATIPA was slightly slower than polyATIPA possibly due to the steric effect of PEG.

In Vivo CT Imaging

Figure 6:
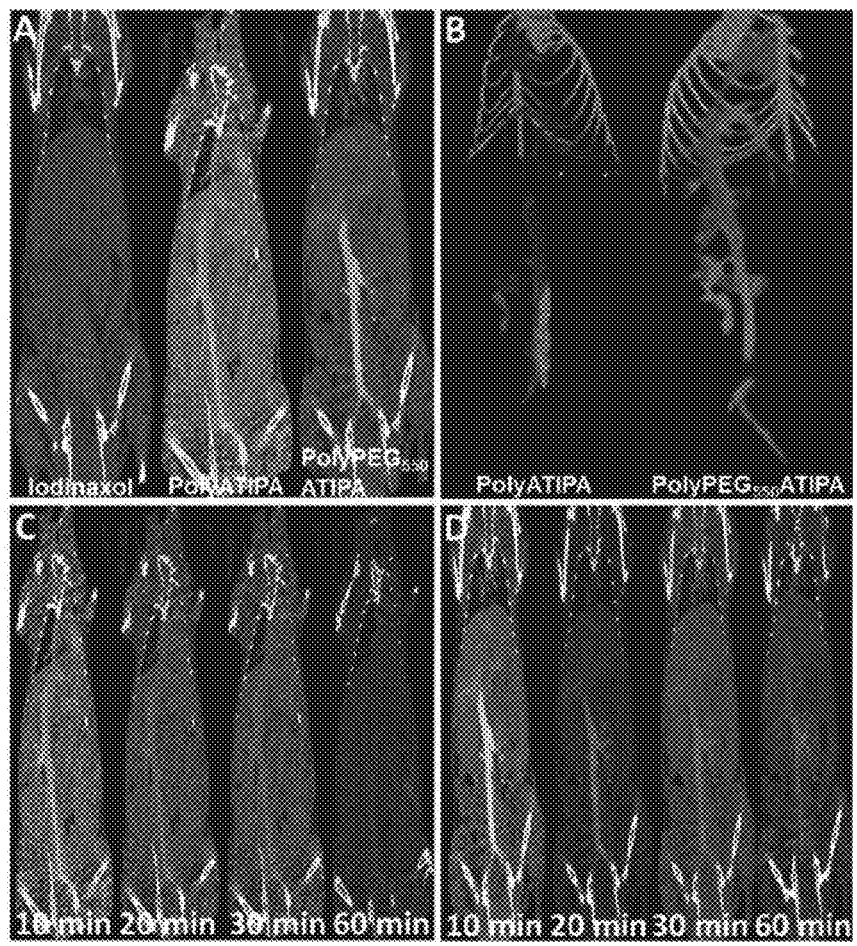
FIG. 6 provides a comparison of in vivo contrast enhanced blood pool CT imaging of iodinaxol, polyATIPA and poly-PEG550ATIPA in Balb/c mice. A, coronal images of mice obtained 10 min after i.v. injection of the agents at a dose of 350 mg-I/kg; B, three-dimensional CT angiogram of the mice contrast enhanced by the polydisulfides at 10 min after i.v. injection. Dynamic contrast enhanced coronal CT images of the mice acquired at 10, 20, 30 and 60 minutes (from left to right) after i.v. injection of polyATIPA (C) and poly-PEG550ATIPA (D) (350 mg-I/kg).

The effectiveness of the iodinated polydisulfides for in vivo contrast enhanced CT imaging was assessed in BALB/c mice (18-22 g body weight, 6 mice per agent) on a micro-CT scanner with iodixanol as a control agent. The iodinated polydisulfides produced strong vascular enhancement and sharp vascular delineation at a dose of 350 mg-I/kg, while the control agent did not produce any enhancement at the same dose and 10 minute after injection due to rapid extravasation and excretion of the agent (FIG. 6). The pegylated agent polyPEG$_{550}$ATIPA resulted in better vascular delineation and less background enhancement than polyATIPA, despite the fact that it had a relatively low in vitro X-ray attenuation at the same dose. PEG in polyPEG$_{550}$ATIPA might decrease non-specific tissue accumulation of the polymers and, consequently, resulted in higher blood concentration for better vascular enhancement than the unpegylated iodinated polydisulfides. Much less non-specific tissue enhancement was also observed for polyPEG$_{550}$ATIPA than polyATIPA.

Dynamic CT imaging revealed that the iodinated polydisulfides showed prolonged blood circulation and vascular enhancement. Signal enhancement was still visible in the mouse aorta at least 30 minutes after the intravascular injection of both agents (FIGS. 6C and D). PolyPEG$_{550}$ATIPA exhibited stronger prolonged vascular enhancement than polyATIPA. Significant vascular enhancement was still visible for polyPEG$_{550}$ATIPA at 60 minutes after the injection. The blood signal increased from 27±30 HU to 526±89 HU at its peak. In comparison, the values for polyATIPA and iodinaxol were 226±67 and 56±26, respectively. PolyPEG$_{550}$ATIPA showed 10 times higher blood pool enhancement than iodinaxol and 2 times higher than polyATIPA. This high enhancement result was comparable to the polymer-coated bismuth contrast agent (Rabin et al., Nat Mater 2006; 5:118-22) and polymer-coated gold contrast agent. Kim et al., J Am Chem Soc 2007; 129 (24): 7661-7665.

Figure 7:
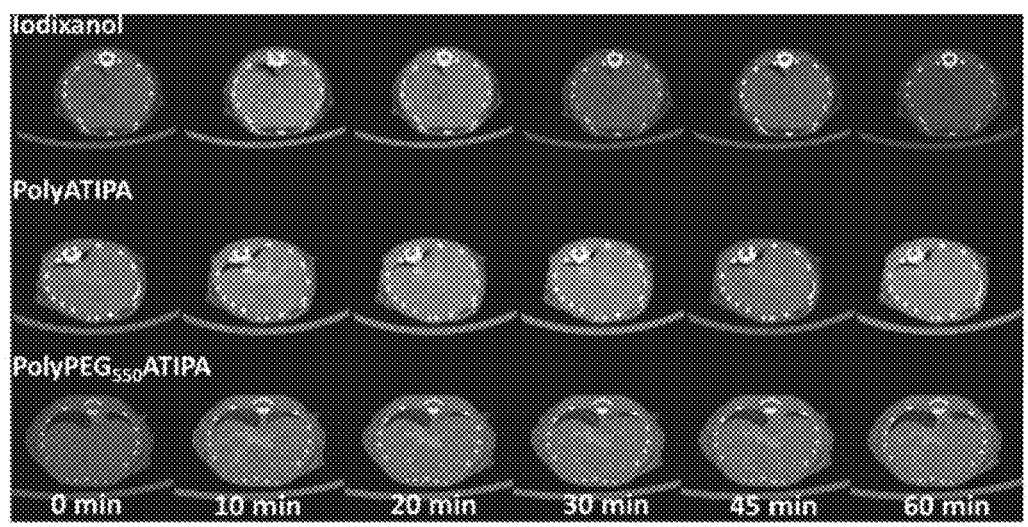
FIG. 7 provides dynamic contrast enhanced axial CT images of the liver of the mice acquired before and at 10, 20, 30 and 60 minutes after i.v. injection of Iodixanol, polyATIPA and polyPEG550ATIPA (350 mg-I/kg).

FIG. 7 shows the representative CT axial images of the liver before and at different time points after contrast with iodinaxol, polyATIPA and polyPEG$_{550}$ATIPA in Balb/c mice. It appears that polyPEG$_{550}$ATIPA resulted in fewer enhancements in the liver tissue than iodinaxol and polyATIPA in Balb/c mice. PolyATIPA had more prolonged liver retention and produced stronger liver enhancement than iodinaxol and polyPEG$_{550}$ATIPA. PEG in polyPEG$_{550}$ATIPA prevented non-specific tissue accumulation of the agent and resulted in minimal liver enhancement. Consequently, the pegylated agent had a prolonged blood circulation and significant enhancement was still visible in the intrahepatic vasculature. The results indicate that the iodinated polydisulfides, especially the pegylated agent, are advantageous for CT blood pool imaging over the clinical agent and polyATIPA. The prolonged blood pool enhancement with minimal background signal is particularly valuable for CT image-guided interventions. The iodinated polydisulfides of the prolonged blood circulation can also have several other clinical applications such as cancer detection and characterizing tumor angiogenesis.

In Vivo Degradation

Figure 8:
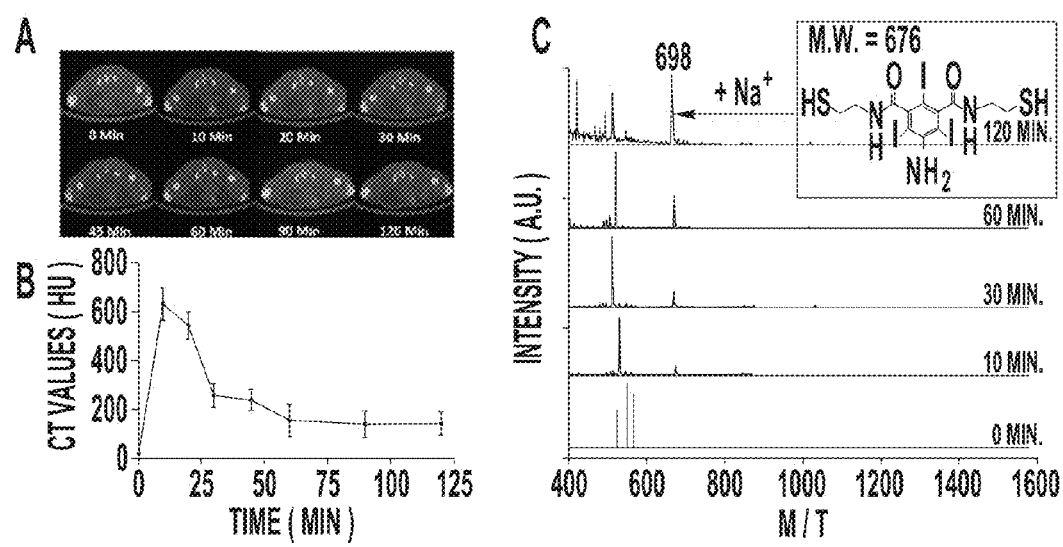
FIG. 8 provides graphs and images showing the detection of in vivo degradation. (A) Serial CT imaging of the bladder (red arrow) of a BALB/c mouse after tail-vein injection with polyATIPA (350 mg-I/kg). (B) Increase of HU in bladder after injection of polyATIPA (350 mg-I/kg). The kinetic curve indicates that the in vivo degradation of polyATIPA is relatively fast (less than 10 min). (C) MALDI-TOF MS traces degradation of in vivo degradation of polyATIPA with the urine of a Balb/c mouse collected at different time points. The increasing intensity of the monomer peak (M.W. 676) suggests polydisulfides can be reduced to oligomers and can be readily excreted via renal filtration.

The in vivo degradation of the iodinated polydisulfides was also investigated using polyATIPA, because the degradation products of polyATIPA excreted in the urine sample were relatively simple and easily to be detected by MALDI-TOF mass spectrometry. Serial CT images of the urinary bladder (arrow, FIG. 8A) showed significant bladder enhancement from 10 to 120 min postinjection of polyATIPA. The images revealed that the contrast agent started clearing out from the body at least 10 minutes after the injection. The dynamic change of the CT values in the bladder was shown in FIG. 8B. It seems that a significant amount of the contrast agent, possibly small molecular weight oligomers, was released in the first 10 minutes postinjection. CT value reduction at 30 minutes was possibly due to urine discharge. The results strongly indicate that the polydisulfide based CT contrast agent was gradually degraded and excreted via renal filtration. The degradation and renal excretion of the iodinated polydisulfides validated the decrease of the blood contrast showed in FIG. 6. FIG. 8C showed the MALDI-TOF mass spectra of the urine samples collected at different time points. The molecular weight of the monomeric units from the reduction of pol-yATIPA (FIG. 8C) was 676. The 698 peak in the spectra corresponded to the unit with a sodium ion. The increasing intensity of the monomer peak over time strongly suggested the contrast agent was eventually degraded into small molecules. These results clearly demonstrated the feasibility of the iodinated polydisulfides as the effective biodegradable macromolecular CT contrast agents.

Histochemical Analysis

Figure 9:
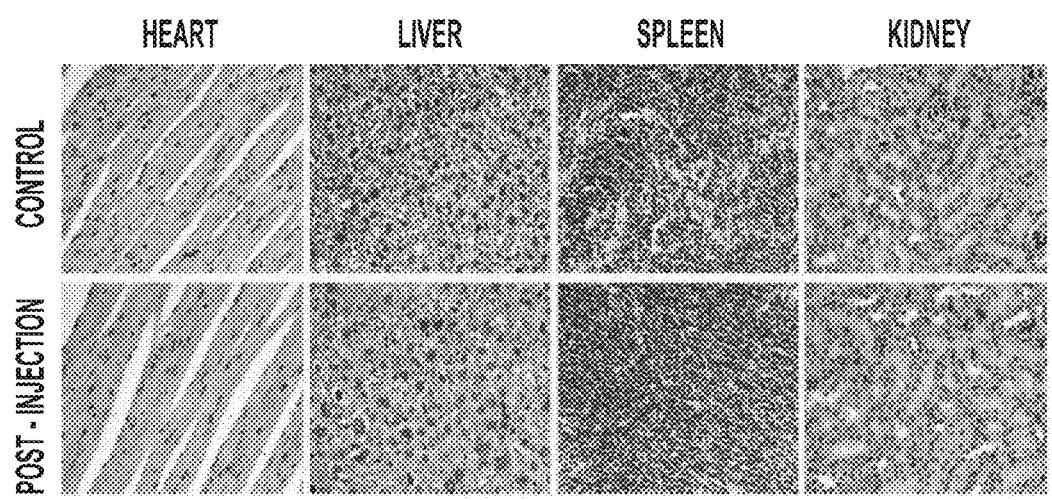
FIG. 9 provides images of histological section of the heart, liver, spleen and kidney of the mouse 1 week after intravenous injection of a single dose (350 mg/Kg) of PolyPEG550ATIPA solution. Sections are stained with H&E and observed under a light microscope at 20× magnification.

Iodinated contrast agents are generally safe in clinical applications. However, exposure of major organs to high doses of iodinated agents may cause tissue damages in some cases. Safety of iodinated polydisulfides is a critical parameter to determine their potential for further translational development. It is appears that poly-PEG$_{550}$ATIPA is a promising biodegradable macro-molecular CT contrast agent because of its superior blood pool contrast enhancement and minimal non-specific tissue accumulation. The safety effect of the agent on the major organs was preliminarily assessed in mice with histochemical analysis. One week after injection of the agent at a dose of 350 mg-I/kg, the mice were sacrificed, and organs of interest (the kidney, liver, spleen, and heart) were collected and fixed in 10% neutral buffered formalin (10% NBF) for haematoxylin and eosin (H&E) staining. The histological images of the organs from the mice injected with the contrast agent were compared with those from the mice injected with PBS (FIG. 9). No significant difference was observed between the mice received with polyPEG$_{550}$ATIPA and PBS, possibly because of minimal non-specific tissue interaction and gradual excretion of the agent via renal filtration. The result suggests that this contrast agent has a good safety profile to these organs.

CONCLUSION

In conclusion, the inventors validated the hypothesis that iodinated polydisulfides are effective bio-degradable macromolecular contrast agents for X-ray CT imaging. The iodinated polydisulfides had prolonged blood circulation and limited vascular extravasation and produced sharp and prolonged vascular delineation. They were more effective for cardiovascular imaging than the clinical agent iodinaxol. Pegylation of the iodinated polydisulfides further improved the blood pool enhancement by reducing non-specific tissue interaction. The high performance of the agents was comparable to the reported heavy metal based agents, e.g. the polymer-coated bismuth contrast agent and polymer-coated gold contrast agent. The pegylated iodinated polydisulfides did not show any observable side effects to the major tissues and organs based on histochemical analysis. The biodegradability, gradual clearance after the imaging and good safety profile are clearly the advantageous features of the iodinated polydisulfides for further clinical development of the agents. Thus, the iodinated polydisulfides are promising biodegradable macromolecular CT contrast agents for cardiovascular and cancer CT imaging and image-guided interventions.

Example 2

Synthesis of polyPEG-ATIPA-Cys

Figure 10:
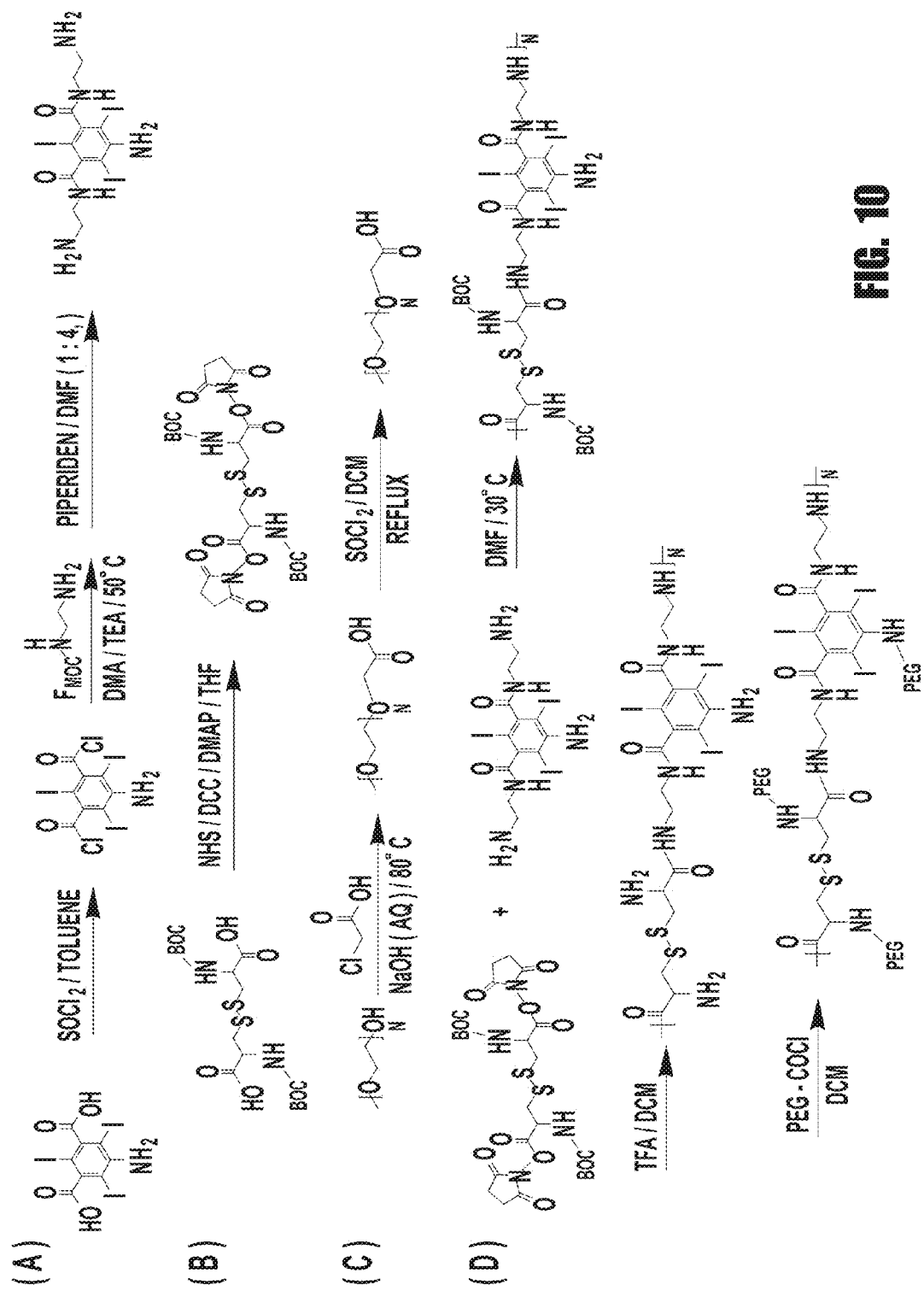
FIG. 10 provides a scheme showing the synthesis of biodegradable polymeric contrast agents including cysteine. A) synthesis of ATIPA diamine; B) synthesis of the monomer of (Boc-cys-NHS)$_2$; C) synthesis of PEGCOCl; D) polymerization of ATIPA diamine with (Box-cys-NHS)$_2$ and modification with PEG550.

A scheme illustrating the steps in the synthesis of polyPEG-ATIPA-Cys is shown in FIG. 10.

Experimental Section

Synthesis of ATIPA Diamine

Ethylene diamine (3 mL) was mixed with 50 mL dimethylacetamide (DMA) at 50° C. under vigorous stirring. Then ATIPC (5 g, ~9 mmol) was completely predissolved in 20 mL DMA at room temperature and dropwise added to above ethylene diamine/DMA solution in 2 h. The reaction continued overnight and the product was purified by precipitating the solution into anhydrous DCM, followed by precipitating in anhydrous ethyl ether after the precipitate was redissolved in DMA at 50° C. Finally the product was dried under reduced pressure. MALDI-TOF (m/z, [M+H]+): 643.45 (obsd.); 642.84 (calcd).

Synthesis of (Boc-cys-NHS)$_2$ (Boc-cys-OH)$_2$ (4.4 g, 10 mmol) and NHS (4.6 g, 40 mmol) were added to 25 mL THF solvent, followed by addition of DCC (8.2 g, 40 mmol) under stifling at room temperature. The reaction continued overnight and the white precipitation (DCU) was filtered off to have clear solution. After concentrated at reduced pressure, the solution was precipitated in anhydrous ethyl ether and the precipitate was washed with ethyl ether twice before the product was dried under reduced pressure. MALDI-TOF (m/z, [M+Na]): 656.82 (obsd.); 634.16 (calcd).

Synthesis of PEGCOCl

PEG550 (11.0 g, 20 mmol) was dissolved in 40 mL 20 wt % NaOH (aq). The solution was stirred strongly and heated up to 85° C. for 30 min. Then chloroacetic acid (9.5 g, 50 mmol) which was predissolved in 20 mL DI water was added dropwise in 0.5 hr. After the reaction continued for 10 hr, the pH value was decreased to around 7 by adding HCl (2 M, aq), washed with water, and dried with anhydrous sodium sulfate and under vacuum. $^1$H NMR (400 MHz, DMSO): δ (ppm): 4.52 (t), 3.37-3.45 (br), 3.18 (s).

PEG550-COOH (6.24 g, 10 mmol) was dissolved in 30 mL anhydrous DCM. Then SOCl$_2$ (5 mL) and one drop of DMF as catalyst were added. The mixture was stirred at room temperature for 20 hr. The residues were removed under vacuum. $^1$H NMR (400 MHz, DMSO): δ (ppm): 4.81 (t), 3.37-3.45 (br), 3.18 (s).

Polymerization of ATIPA Diamine with (boc-cys-NHS)$_2$

ATIPA diamine (64.3 mg, 0.1 mmol) and (Boc-cys-NHS)$_2$ (63.4 mg, 0.1 mmol) was dissolved in 1 mL DMA at 40° C. under vigorous stifling and the reaction continued overnight. The polymer was precipitated in ethyl ether and dried under reduced pressure. (yield: 95%).

Modification of PEG-ATIPC-Cys with PEG550

After removal of Boc protection in PEG-ATIPC-Cys in TFA, PEG-ATIPC-Cys (0.1 mmol) and PEGCOCl (0.3 mmol) were dissolved in DMA at 35° C. After 200 µL TEA was added, the reaction continued overnight. The polymer was purified through precipitating the crude product in cold ethyl ether. $^1$H NMR (400 MHz, DMSO): δ (ppm): 4.82 (t), 4.22 (t), 3.37-3.45 (br), 3.18 (s), 2.96 (d).

Characterizations $^1$H NMR spectra were obtained on a 600 MHz Varian Inova NMR spectrometer with deuterated solvent (DMSO-d6). MALDI-TOF mass spectra were acquired on a MALDI-TOF mass spectrometer (Autoflex™ Speed, Bruker) in a linear mode with 2,5-dihydroxybenzoic acid (2,5-DHB) as a matrix. The molecular weight of polyPEG-ATIPA-Cys was determined with size exclusion chromatography (SEC) on an AKTA FPLC system (Amersham Biosciences Corp., Piscataway, N.J.) equipped with a Superose 12 column and a refractive index detector. Molecular weights were calibrated with standard poly[N-(2-hydroxypropyl)methacrylamide]. Ion-pairing reverse-phase HPLC (Agilent 1100, Santa Clara, Calif.) was performed with a RP-C18 HPLC column (4.6×250 mm2, 5 µm particle size) and UV detector. The mobile phase was a gradient acetonitrile aqueous solution (10-50%) containing 0.5% TFA at a total flow rate of 1 mL/min. An aliquot of 200 µL sample at approximately 0.1 mg/mL was injected. The UV absorption at 210 nm was recorded for analysis.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A biodegradable macromolecular computed tomography (CT) contrast agent comprising a polyiodinated aryl contrast agent having a structure according to formula I:

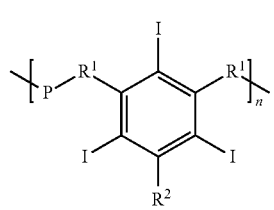

wherein P is an organic disulfide, R$^1$ is a carboxyl or carboxamide group, and R$^2$ is a an amine, a lower alkyl group, or an amine-bound water soluble polymer or oligomer, and n is from 2 to 10,000 or a structure according to formula II:

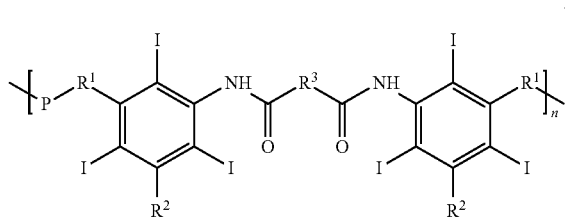

wherein P is an organic disulfide, R$^1$ is a carboxyl or carboxamide group, and R$^2$ is a an amine, a lower alkyl group, or an amine-bound water soluble polymer or oligomer, R$^3$ is a lower alkylene or alkylene ether group, and n is from 2 to 10,000.

2. The biodegradable macromolecular CT contrast agent of claim 1, wherein the polyiodinated aryl contrast agent is PEGylated.

3. The biodegradable macromolecular CT contrast agent of claim 1, wherein $R^2$ is an amine.

4. The biodegradable macromolecular CT contrast agent of claim 1, wherein $R^1$ is a carboxamide group.

5. The biodegradable macromolecular CT contrast agent of claim 1, wherein the contrast agent has a structure according to formula III:

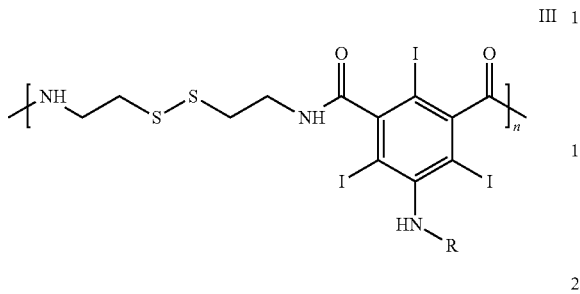

wherein R is a water soluble polymer or oligomer, and n is from 2 to 10,000.

6. The biodegradable macromolecular CT contrast agent of claim 1, wherein the contrast agent has a structure according to formula IV:

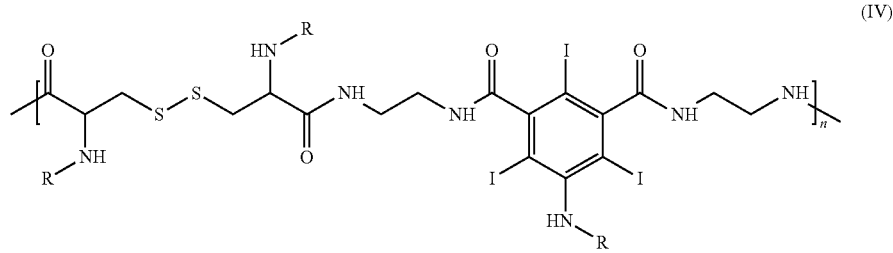

wherein R is a water soluble polymer or oligomer and n is from 2 to 10,000.

7. A method for imaging a tissue region of a subject comprising:
(a) administering an effective amount of a biodegradable macromolecular computed tomography (CT) contrast agent according to claim 1 to the subject;
(b) allowing a sufficient amount of time for the macromolecular biodegradable CT contrast agent to enter the tissue region; and
(c) performing x-ray computed tomography imaging of the tissue region of the subject.

8. The method of claim 7, wherein $R^2$ is a an amine.

9. The method of claim 7, wherein $R^1$ is a carboxamide group.

10. The method of claim 7 wherein the biodegradable macromolecular CT contrast agent has a structure according to formula III:

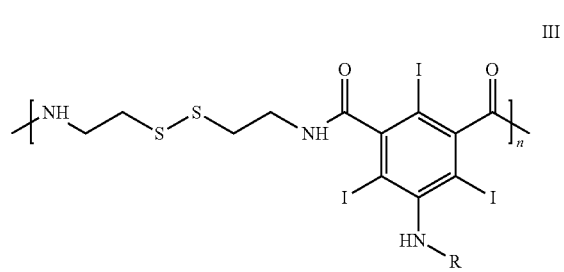

wherein R is a water soluble polymer or oligomer, and n is from 2 to 10,000.

11. The method of claim 7, wherein the biodegradable macromolecular CT contrast agent has a structure according to formula IV:

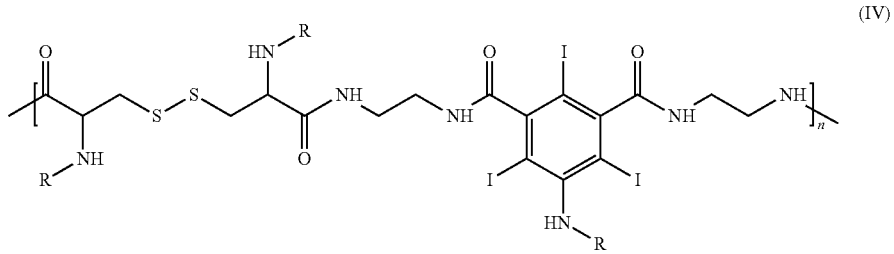

wherein R is a water soluble polymer or oligomer, and n is from 2 to 10,000.

12. The method of claim 7 wherein the tissue region is a blood vessel.

13. The method of claim 7, wherein the tissue region is a tumor.

14. A method of making a biodegradable computed tomography (CT) contrast agent, comprising the steps of:
   (a) reacting pegylated or non-pegylated 5-amino-2,4,6-triiodoisophthalic acid (ATIPA) with thionyl chloride to provide an diacyl chloride polyiodinated aryl group; and
   (b) polymerizing the diacyl chloride iodinated aryl group with an organic disulfide to provide a polyiodinated aryl contrast agent that is crosslinked by an organic disulfide.

15. The method of claim 14, wherein the dicarboxyl polyiodinated aryl group is 5-amino-2,4,6-triiodoisophthalic acid (ATIPA).

16. The method of claim 14, wherein the dicarboxyl polyiodinated aryl group is PEGylated 5-amino-2,4,6-triiodoisophthalic acid (ATIPA).

* * * * *